(12) United States Patent
Tanaka et al.

(10) Patent No.: US 8,308,635 B2
(45) Date of Patent: Nov. 13, 2012

(54) ENDOSCOPE SYSTEM

(75) Inventors: Hideki Tanaka, Tama (JP); Jun Hasegawa, Hino (JP); Toshio Nakamura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1008 days.

(21) Appl. No.: 12/330,994

(22) Filed: Dec. 9, 2008

(65) Prior Publication Data
US 2009/0149711 A1   Jun. 11, 2009

(30) Foreign Application Priority Data

Dec. 10, 2007   (JP) .................................. 2007-318658

(51) Int. Cl.
*A61B 1/00* (2006.01)
(52) U.S. Cl. ........................................................ 600/152
(58) Field of Classification Search .................. 600/117, 600/145, 146, 152
See application file for complete search history.

(56) References Cited

U.S. PATENT DOCUMENTS

| | | | |
|---|---|---|---|
| 5,658,238 A | 8/1997 | Suzuki et al. | |
| 6,295,368 B1 * | 9/2001 | Hasegawa et al. | 382/128 |
| 2007/0112255 A1 * | 5/2007 | Ikeda et al. | 600/146 |
| 2007/0149852 A1 * | 6/2007 | Noguchi et al. | 600/144 |
| 2007/0173694 A1 * | 7/2007 | Tsuji et al. | 600/146 |
| 2008/0045794 A1 * | 2/2008 | Belson | 600/145 |
| 2009/0048488 A1 * | 2/2009 | Uchimura | 600/152 |
| 2009/0299136 A1 * | 12/2009 | Hasegawa et al. | 600/106 |
| 2010/0298641 A1 * | 11/2010 | Tanaka | 600/109 |
| 2011/0237889 A1 * | 9/2011 | Tanaka | 600/118 |

FOREIGN PATENT DOCUMENTS

| | | |
|---|---|---|
| CN | 101026988 A | 8/2007 |
| EP | 1 800 593 A1 | 6/2007 |
| EP | 1 818 005 A1 | 8/2007 |
| EP | 1 884 185 A1 | 2/2008 |
| JP | 07-000346 | 1/1995 |
| JP | 2006-192056 | 7/2006 |
| JP | 2007-054307 | 3/2007 |
| WO | WO 2007/023631 A1 | 3/2007 |

\* cited by examiner

*Primary Examiner* — Rodney Fuller
(74) *Attorney, Agent, or Firm* — Scully, Scott, Murphy & Presser, P.C.

(57) ABSTRACT

An endoscope system includes an endoscope with a bending portion installed on a distal side of an insertion portion; a bending drive unit which drives and bends the bending portion electrically; a map information storage unit which stores map information digitized by associating an amount of bending and a corresponding three-dimensional position and direction of a distal end of the insertion portion with each other, with a position near a rear end of the bending portion being designated as a reference position; a position and direction detecting unit which detects the position and direction of the distal end of the insertion portion; and a bending control unit which controls the bending drive unit to orient the distal end of the insertion portion into a target direction using the map information.

20 Claims, 13 Drawing Sheets

INSERTION SHAPE DATA

FRAME DATA

COIL COORDINATES

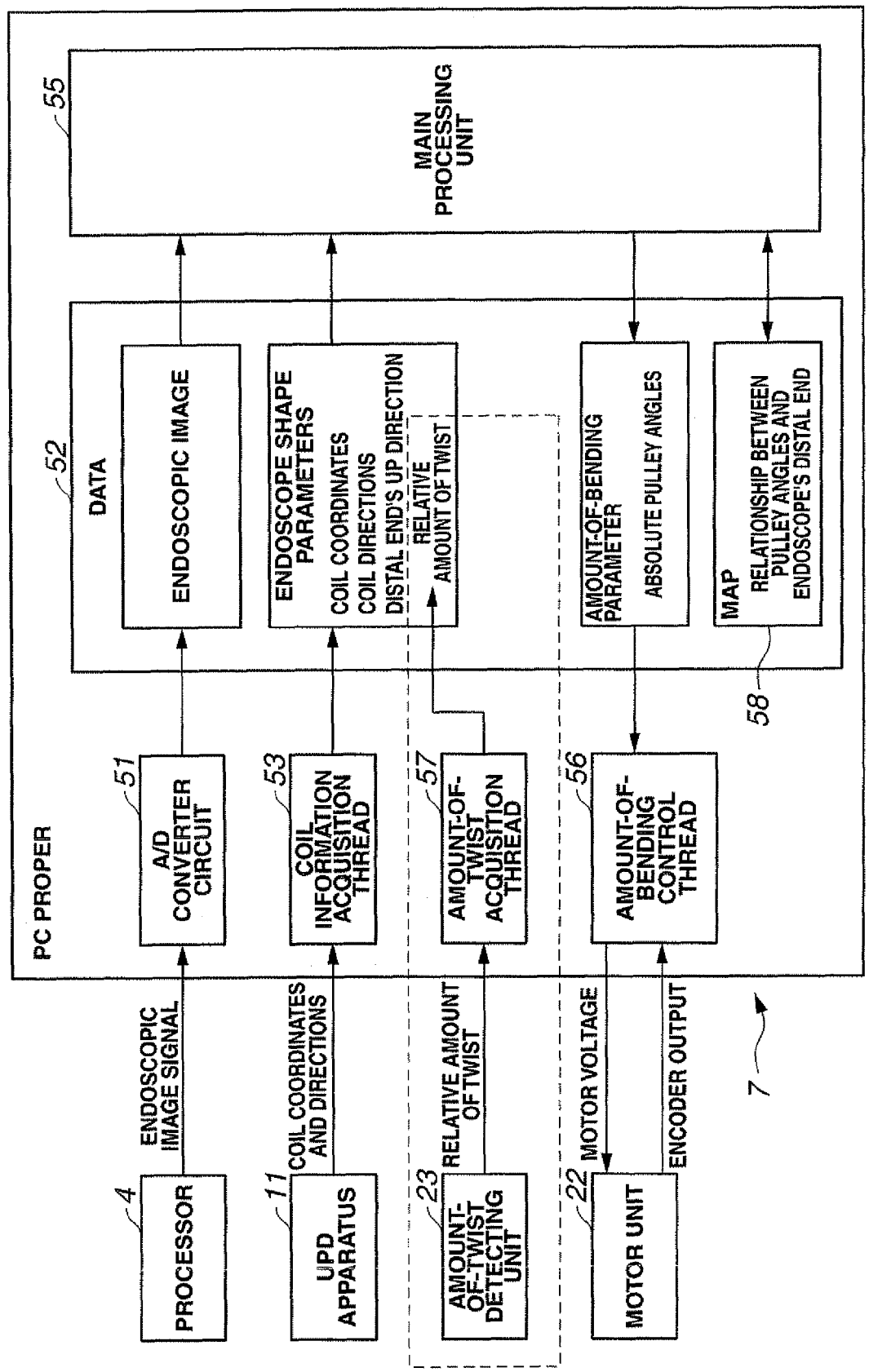

ENDOSCOPE SYSTEM

This application claims benefit of Japanese Application No. 2007-318658 filed in Japan on Dec. 10, 2007, the contents of which are incorporated herein by this reference.

BACKGROUND OF THE INVENTION

1. Field of the Invention

The present invention relates to an endoscope system used to conduct endoscopy with an endoscope inserted in a subject.

2. Description of the Related Art

Recently, endoscopes have come into wide use in the field of medicine. The endoscopes have an elongated insertion portion which is inserted into a subject. A bending portion configured to be bendable is installed on a distal side of the insertion portion.

The bending portion of the endoscope is operated by pulling and relaxing a wire from a rear side of the insertion portion, but there are also motor-operated endoscopes which operates the bending portion using driving force of a motor serving as bending drive means to improve operability of the bending portion.

However, when conducting endoscopy in a crooked body cavity such as an intestinal tract, it is difficult for an inexperienced surgeon to move a distal end of the endoscope to a target position and pass through a target line (e.g., a center line of the intestinal tract).

To deal with this, there is an endoscope system which determines, based on endoscopic images, in what direction the distal end of the endoscope should be directed (e.g., toward a dark part), determines a target position for the distal end of the endoscope based on the direction thus determined, and performs bending operations to bring current position of the endoscope's distal end into coincidence with the target position for the distal end of the endoscope.

On the other hand, Japanese Patent Application Laid-Open Publication No. 2006-192056 discloses an endoscope control unit which includes a bending operation storage means which stores bending operations of a bending portion; and parameter storage means which prestores operation parameters corresponding to the bending operations of the bending portion, wherein the endoscope control unit controls an amount of bending of the bending portion by retrieving an operation parameter corresponding to a bending operation of the bending portion from the parameter storage means.

The parameter storage means stores data on a total number n of bend commands, counted from immediately after production of the endoscope system, given by a bend command input means with respect to which direction to operate the bending portion, up, down, left, or right.

The conventional example discloses a technique for performing bending operations using settings information which, being prestored in memory, represents pulse widths (of a drive signal) corresponding to different numbers of bends.

SUMMARY OF THE INVENTION

An endoscope system according to one aspect of the present invention includes: an endoscope in which a bending portion configured to be bendable is installed on a distal side of an insertion portion; a bending drive unit which drives and bends the bending portion electrically; a map information storage unit which stores map information digitized by associating an amount of bending, including a bending direction, produced when the bending portion is bent and a three-dimensional position and direction of a distal end of the insertion portion corresponding to the amount of bending with each other, with a position near a rear end of the bending portion on the distal side of the insertion portion being designated as a reference position; a position and direction detecting unit which detects the three-dimensional position and direction of the distal end of the insertion portion; and a bending control unit which controls electrically-driven bending performed by the bending drive unit so as to orient the distal end of the insertion portion into a target direction using the map information.

An endoscope system according to another aspect of the present invention includes: an endoscope which includes an insertion portion equipped with a bending portion configured to be bendable; a map information storage unit which stores map information digitized about a locus of a three-dimensional position and direction of a distal end of the insertion portion generated when the bending portion is bent, with a position near a rear end of the bending portion being designated as a reference position; a direction-of-the-distal-end calculating unit which calculates a current direction of the distal end of the insertion portion using the map information when a current three-dimensional position of the distal end of the insertion portion is specified; a direction-of-the-target-position calculating unit which calculates a direction of the target position into which the distal end of the insertion portion is to be oriented using the map information; and a bending control unit which bends the bending portion to move the distal end from the current position toward the target position based on calculation results produced by the direction-of-the-distal-end calculating unit and the direction-of-the-target-position calculating unit.

BRIEF DESCRIPTION OF THE DRAWINGS

FIG. 7 is a diagram showing a function block configuration of a PC proper;

DETAILED DESCRIPTION OF THE PREFERRED EMBODIMENTS

A preferred embodiment of the present invention will be described below with reference to the drawings.

Figure 1:
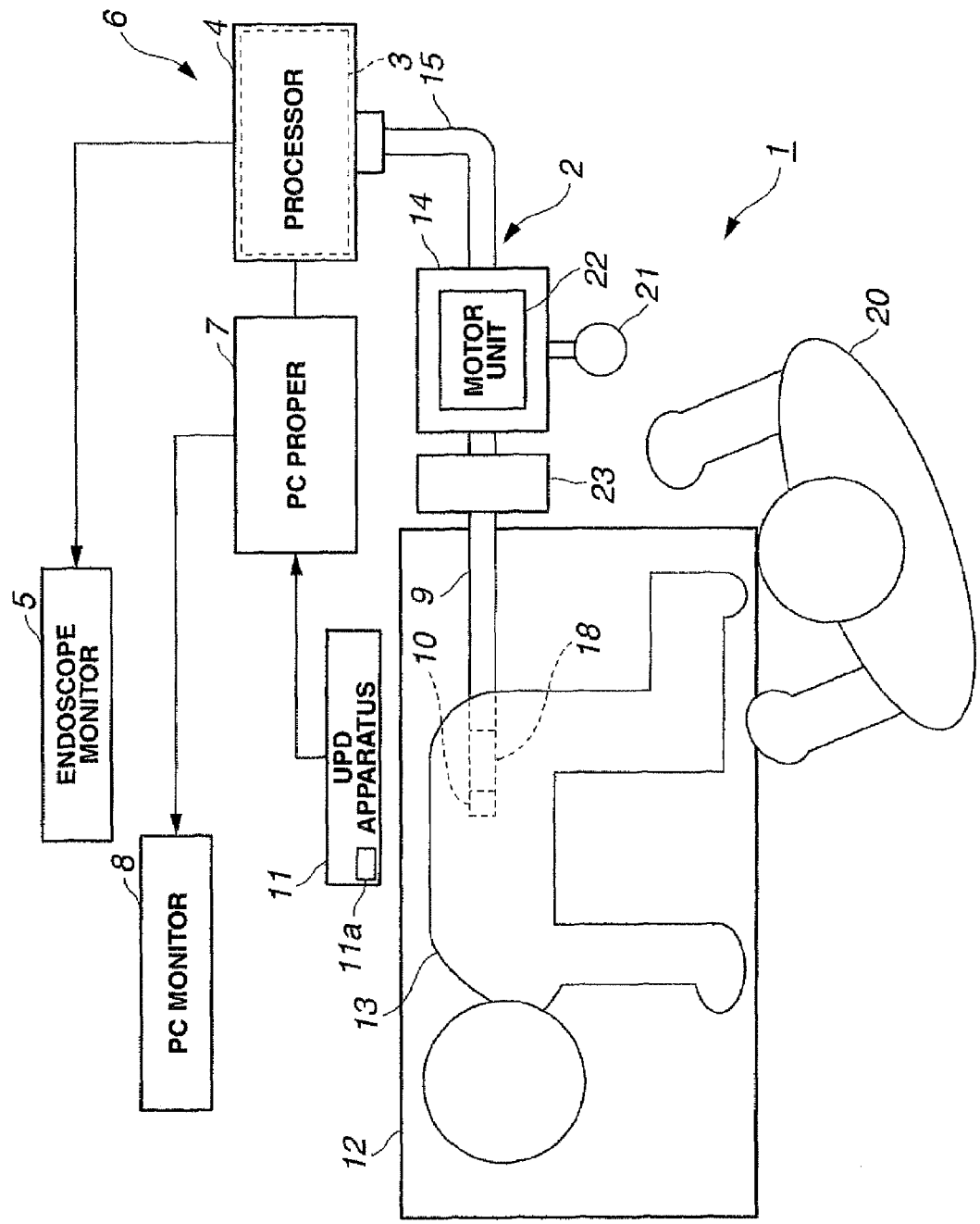
FIG. 1 is a diagram showing a configuration of an endoscope system according to a first embodiment of the present invention under exemplary conditions of use.
Figure 2:
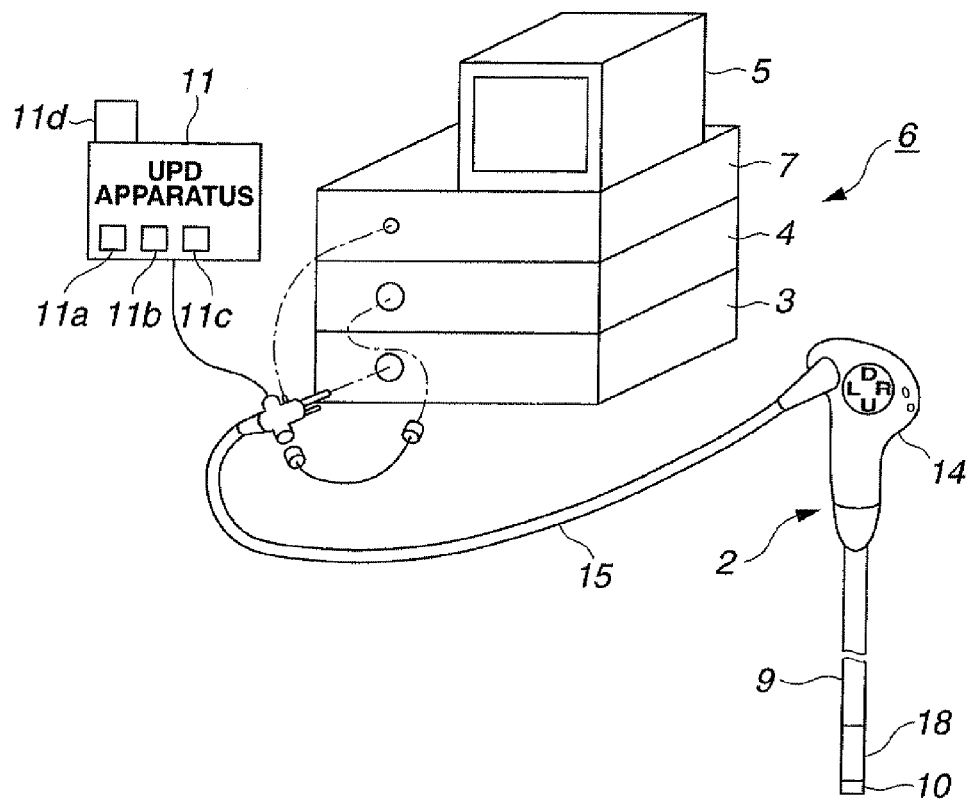
FIG. 2 is a diagram showing an exemplary appearance of an endoscope apparatus.
Figure 3:
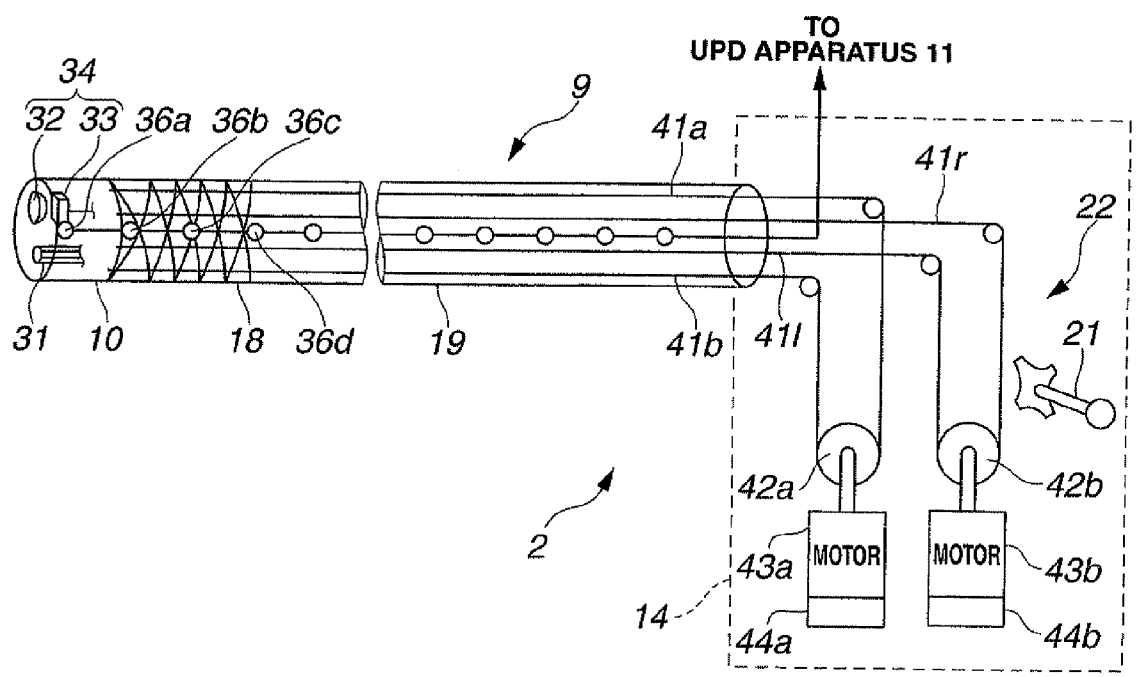
FIG. 3 is a diagram showing an internal configuration of an endoscope.
Figure 4:
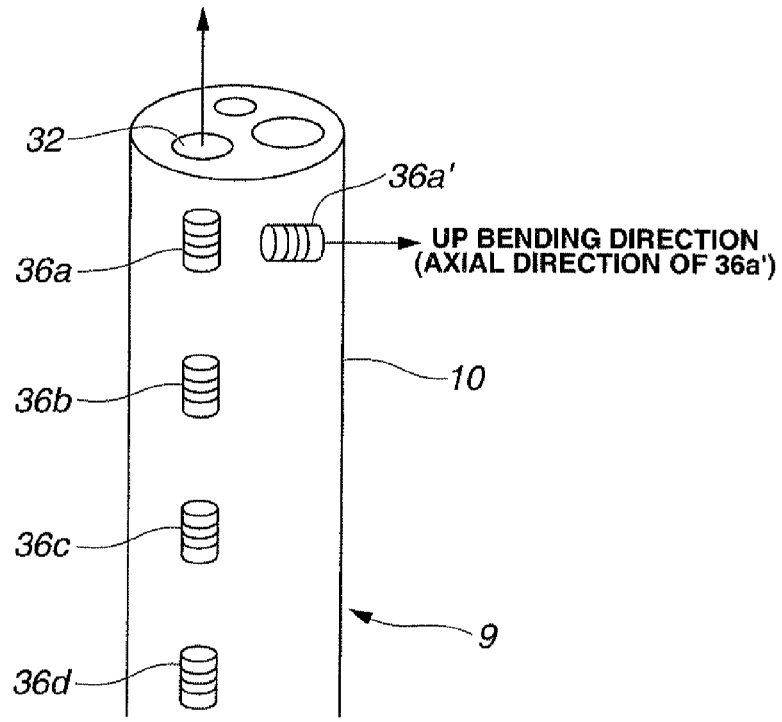
FIG. 4 is a diagram showing an exemplary arrangement of coils on a distal side of an insertion portion.
Figure 5:
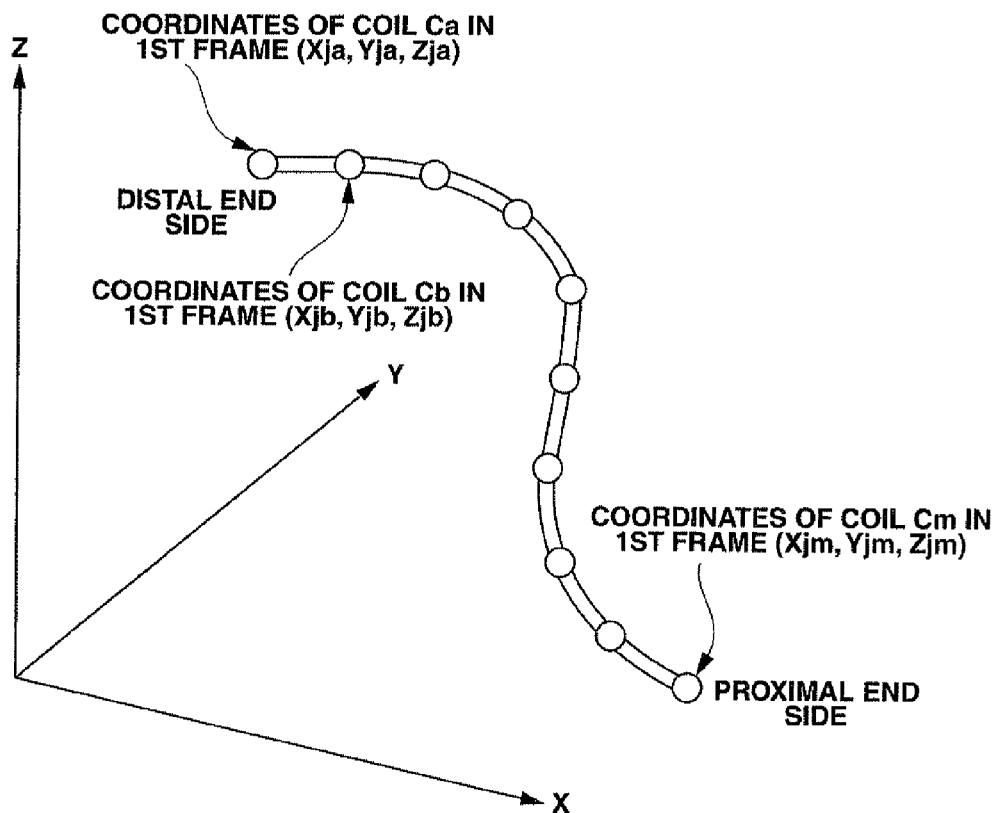
FIG. 5 is a diagram showing a detected insertion shape.

FIGS. 1 to 18 relate to a first embodiment of the present invention. FIG. 1 shows a configuration of an endoscope system according to the first embodiment of the present invention under exemplary conditions of use, FIG. 2 shows an exemplary appearance of an endoscope apparatus, FIG. 3 shows an internal configuration of an endoscope, FIG. 4 shows an exemplary arrangement of coils on a distal side of an insertion portion, and FIG. 5 shows a detected insertion shape.

Figure 6A:
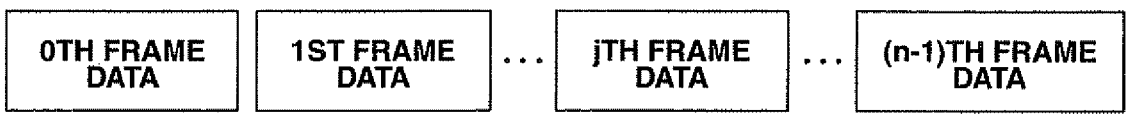
FIG. 6A is a diagram showing exemplary insertion shape data.
Figure 6B:
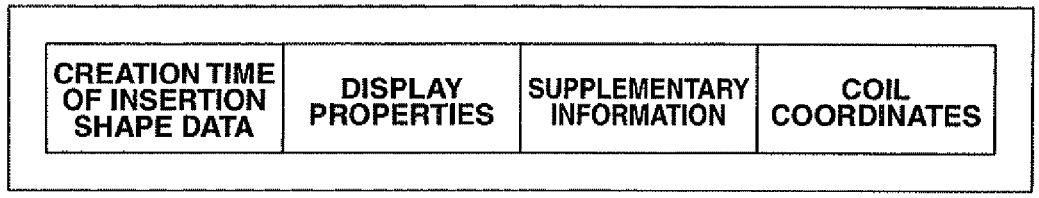
FIG. 6B is a diagram showing exemplary frame data.
Figure 6C:
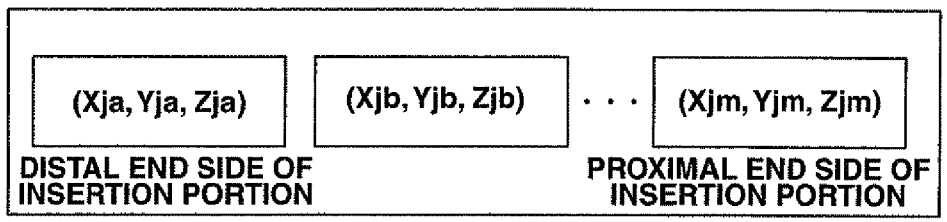
FIG. 6C is a diagram showing exemplary coil coordinate data.
Figure 8:
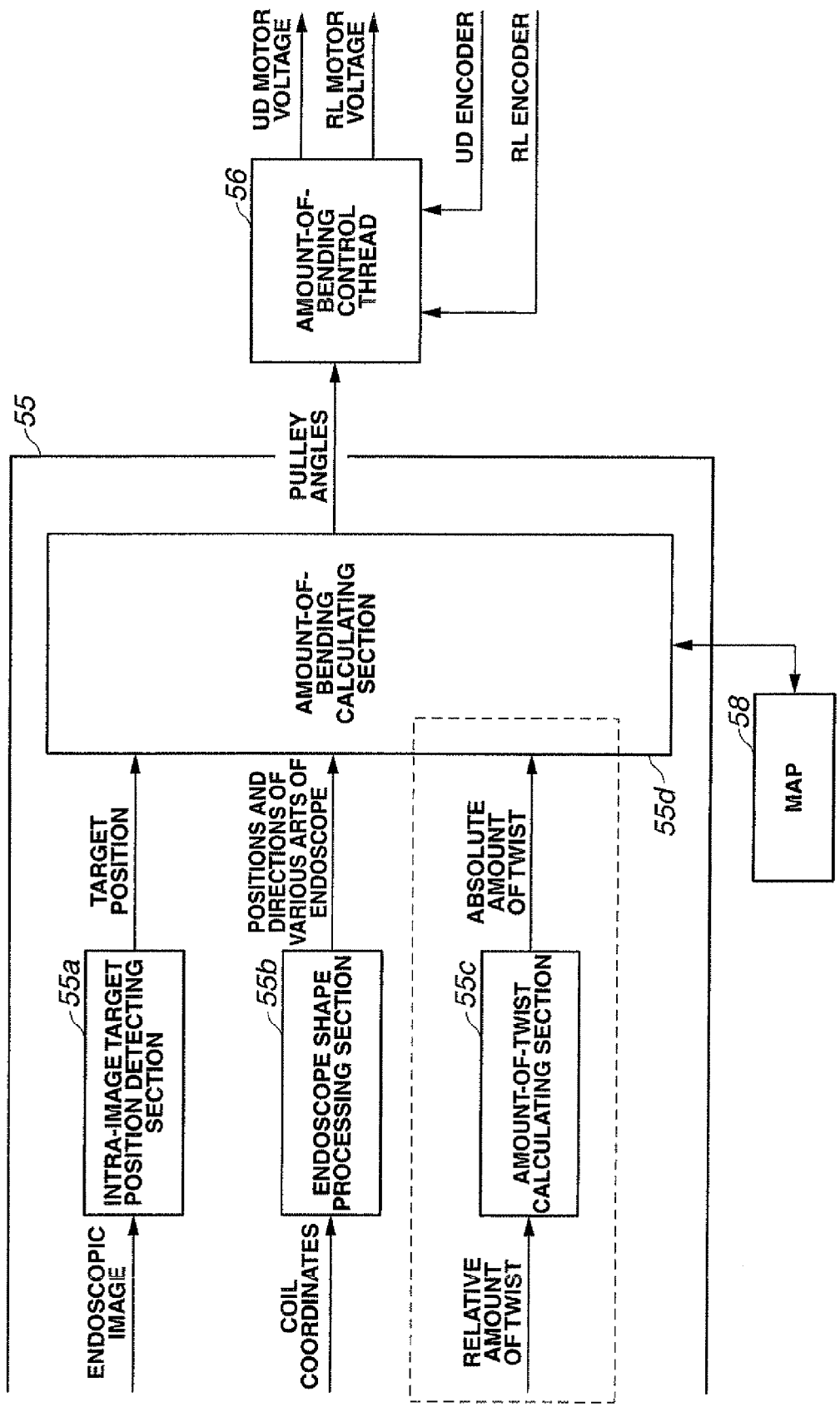
FIG. 8 is a diagram showing a function block configuration of a main processing unit.
Figure 9:
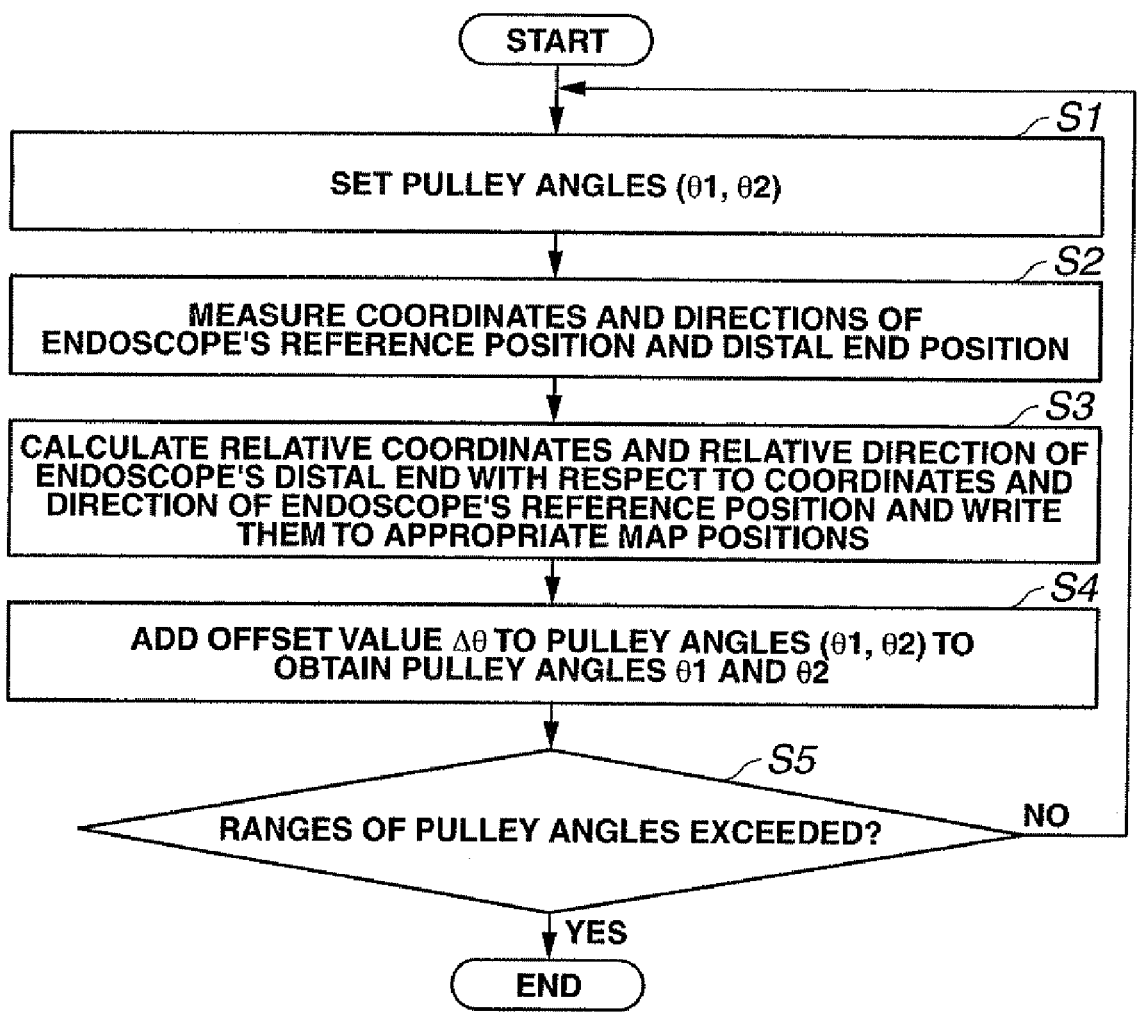
FIG. 9 is a flowchart of processing procedures for creating a map.
Figure 10:
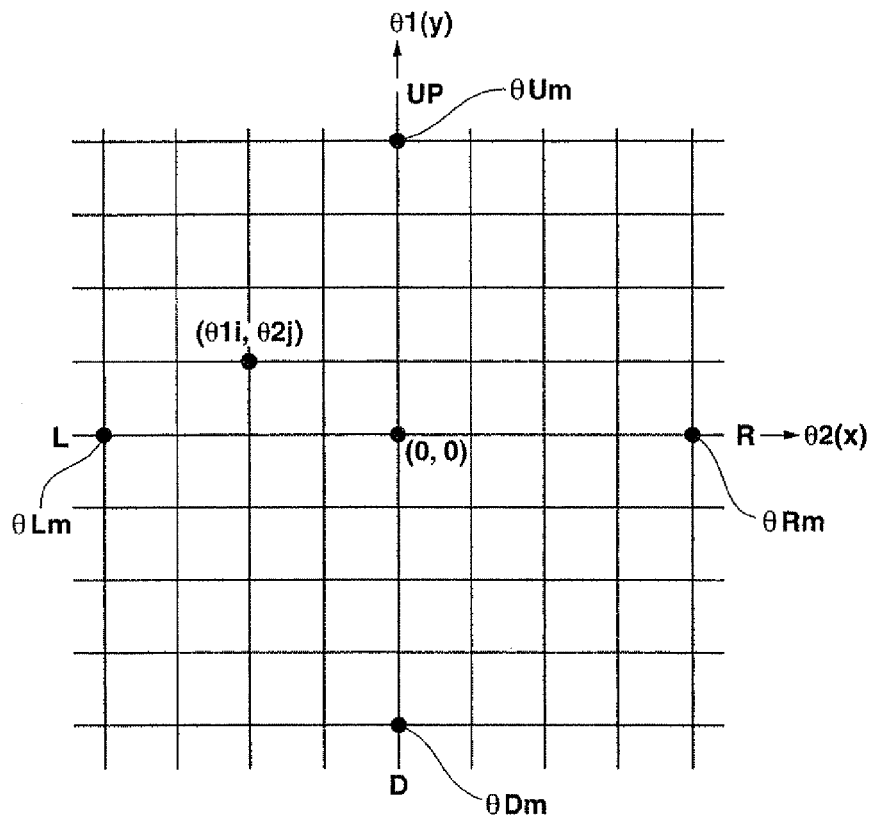
FIG. 10 is an explanatory diagram showing how map data is created.

FIGS. 6A to 6C show exemplary insertion shape data, exemplary frame data, and exemplary coil coordinate data, FIG. 7 shows a function block configuration of a PC proper, FIG. 8 shows a function block configuration of a main processing unit, FIG. 9 shows processing procedures for creating a map, and FIG. 10 illustrates how map data is created.

Figure 11:
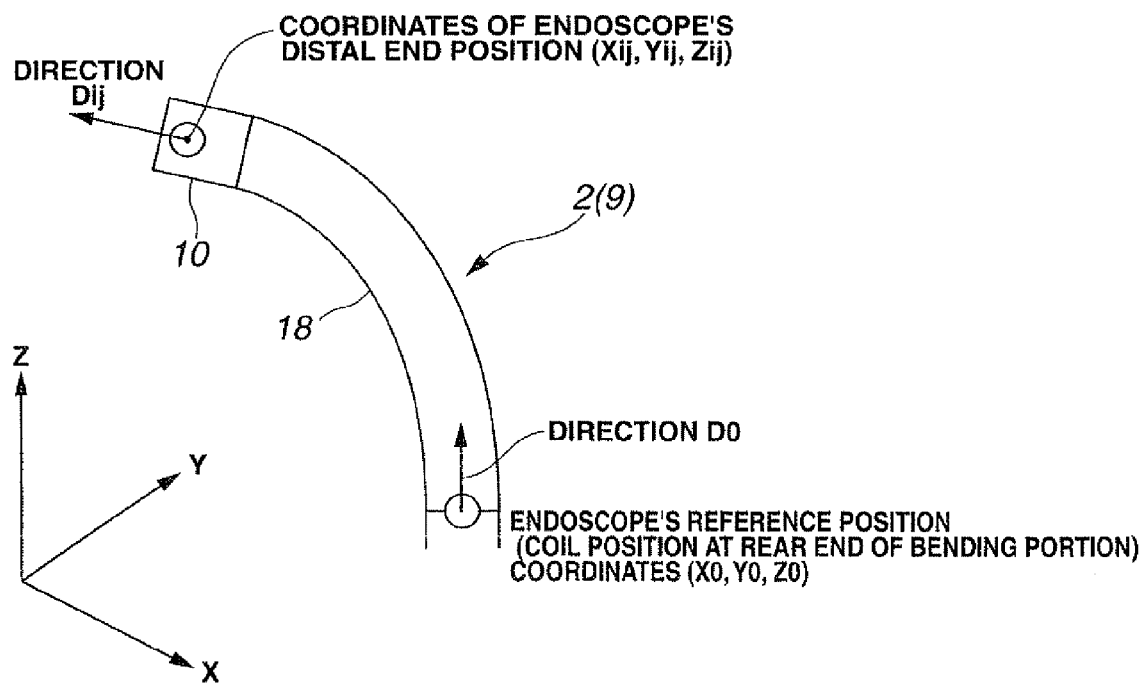
FIG. 11 is an explanatory diagram showing coordinates and the like of an endoscope's reference position and distal end when a map is created.
Figure 12A:
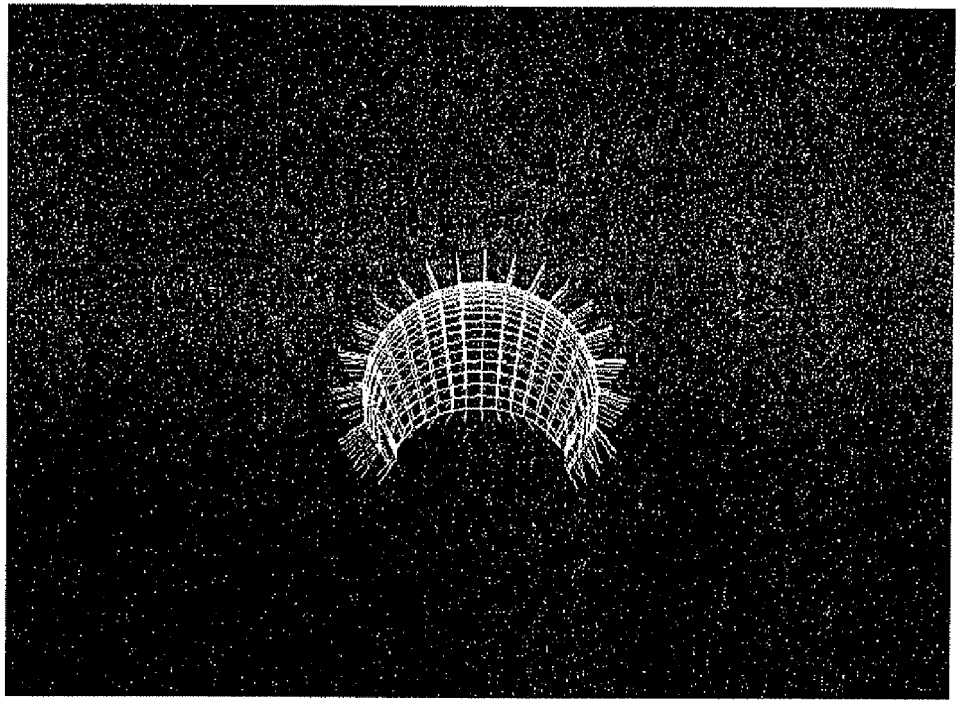
FIG. 12A is a side view of the map expressed in a three-dimensional coordinate system at the distal end of the endoscope, as viewed from below upward in a direction of bending.
Figure 12B:
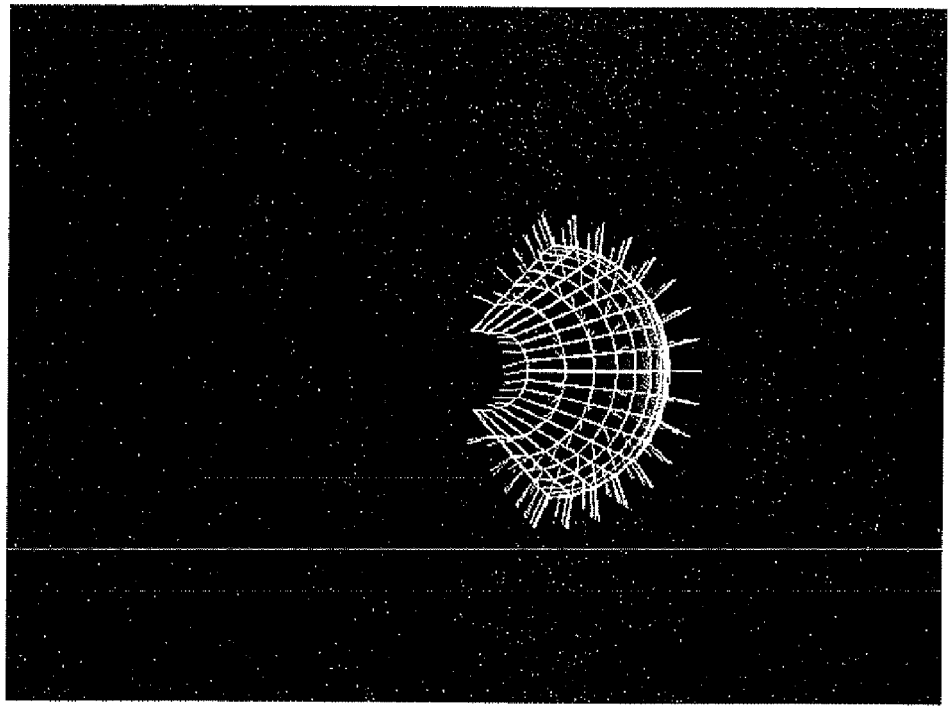
FIG. 12B is a side view of the map expressed in the three-dimensional coordinate system at the distal end of the endoscope, as viewed from right to left in the direction of bending.
Figure 13:
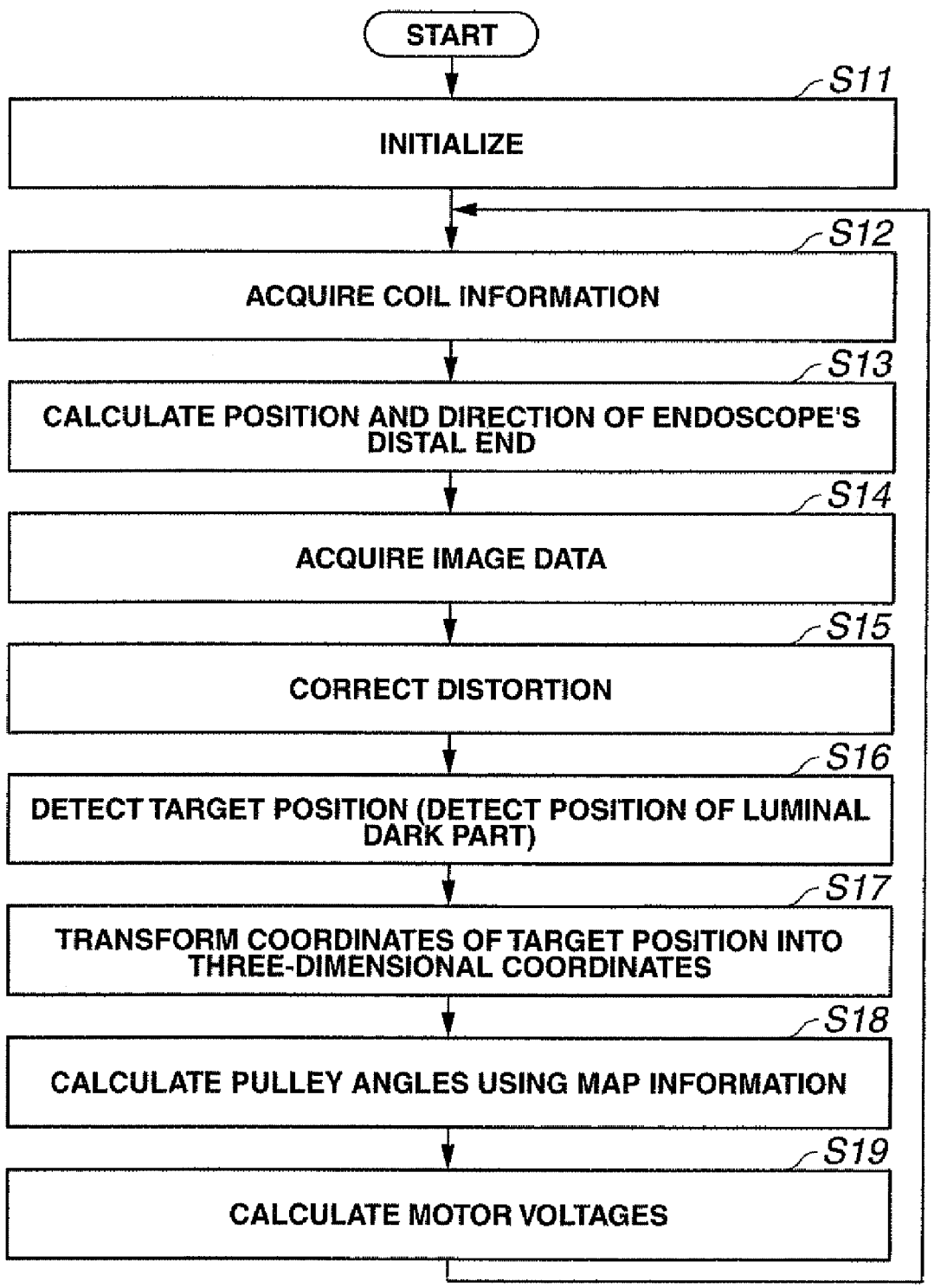
FIG. 13 is a flowchart showing bending control procedures according to the present embodiment.
Figure 14:
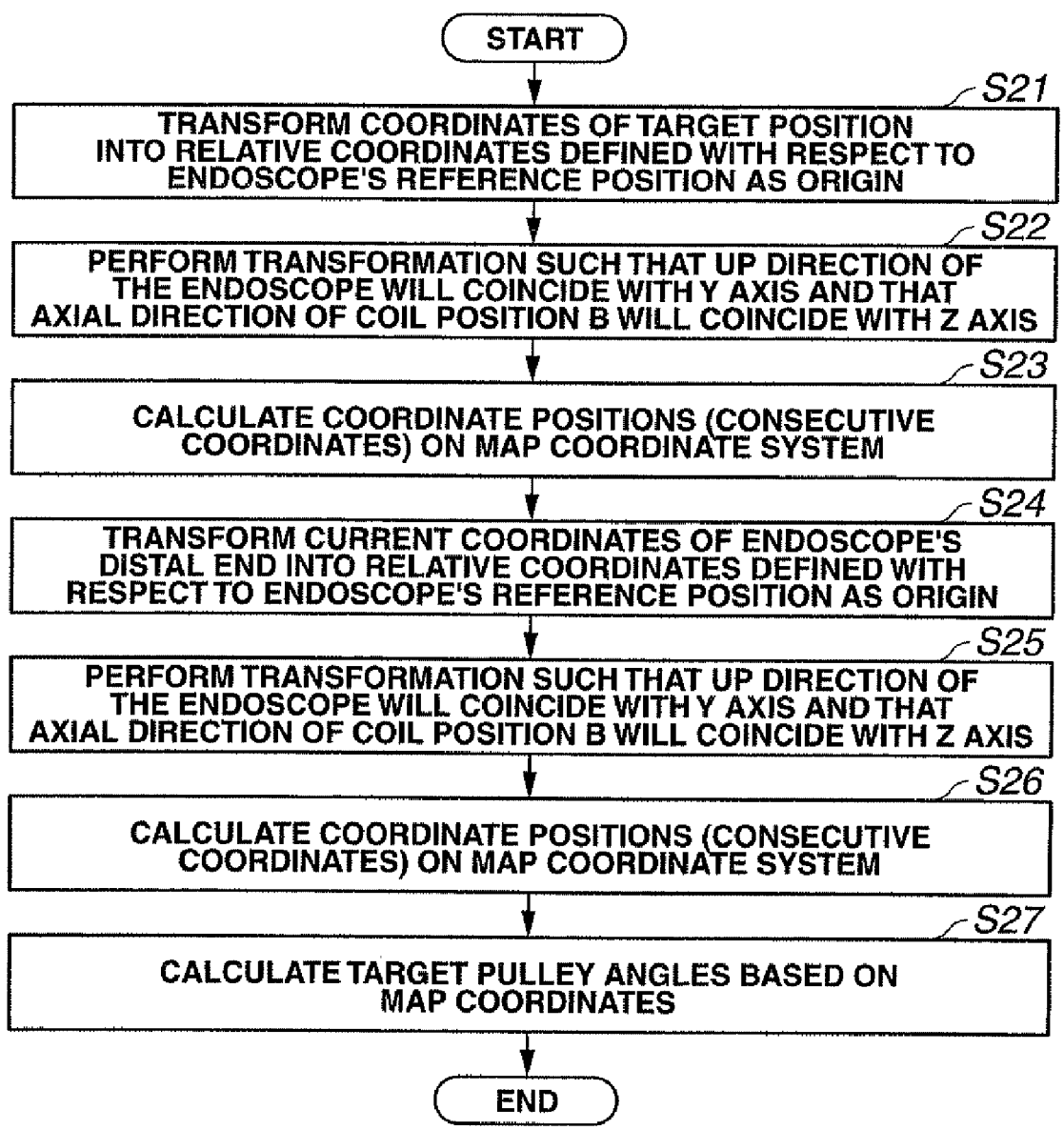
FIG. 14 is a flowchart showing procedures for calculating target pulley angles using map information.

FIG. 11 shows coordinates and the like of an endoscope's reference position and distal end when a map is created, FIGS. 12A and 12B show the generated map three-dimensionally, FIG. 13 shows bending control procedures according to the present embodiment, and FIG. 14 shows procedures for calculating target pulley angles using map information.

Figure 15:
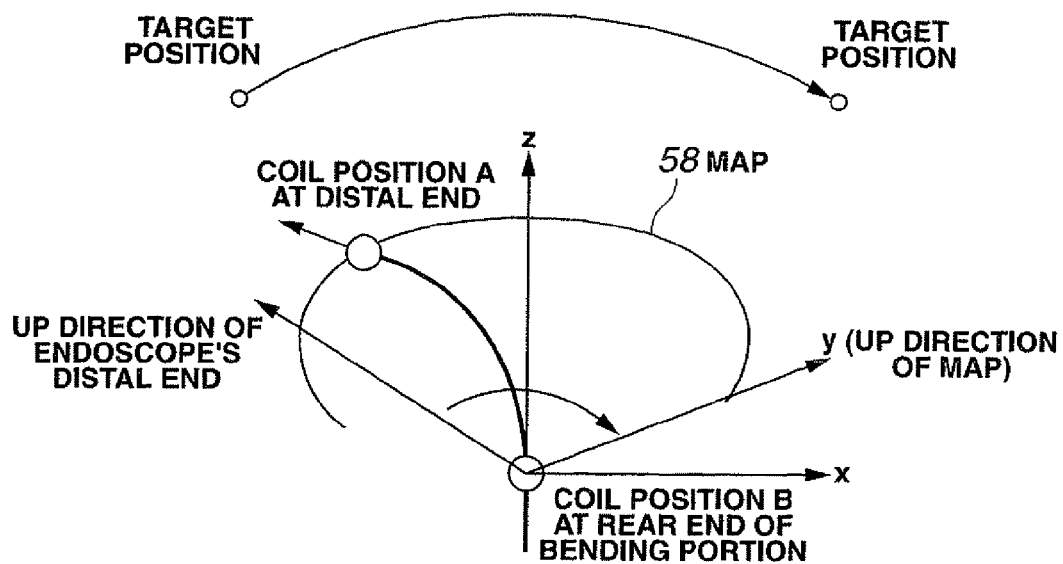
FIG. 15 is an explanatory diagram showing how an Up direction of the distal end of the endoscope is made to coincide with a y-axis direction.
Figure 16:
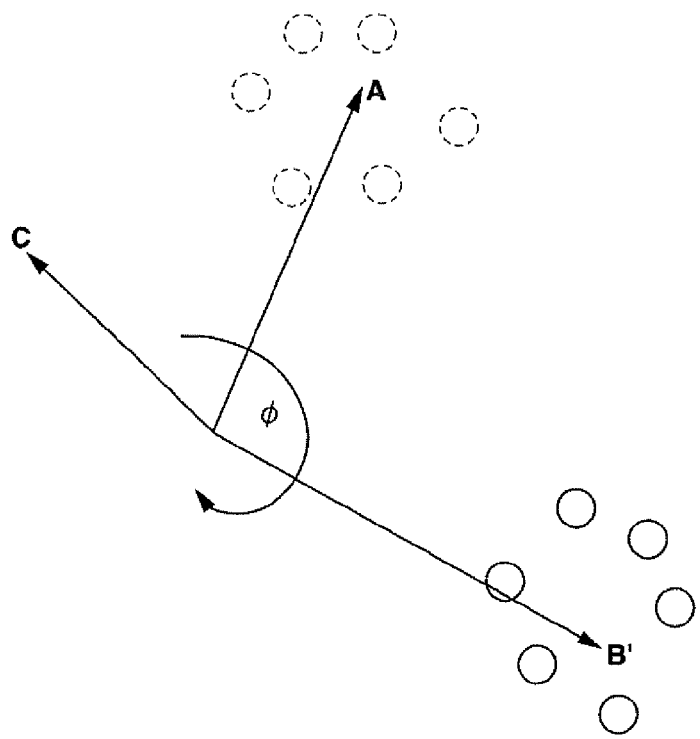
FIG. 16 is an explanatory diagram showing how a quaternion is used.
Figure 17:
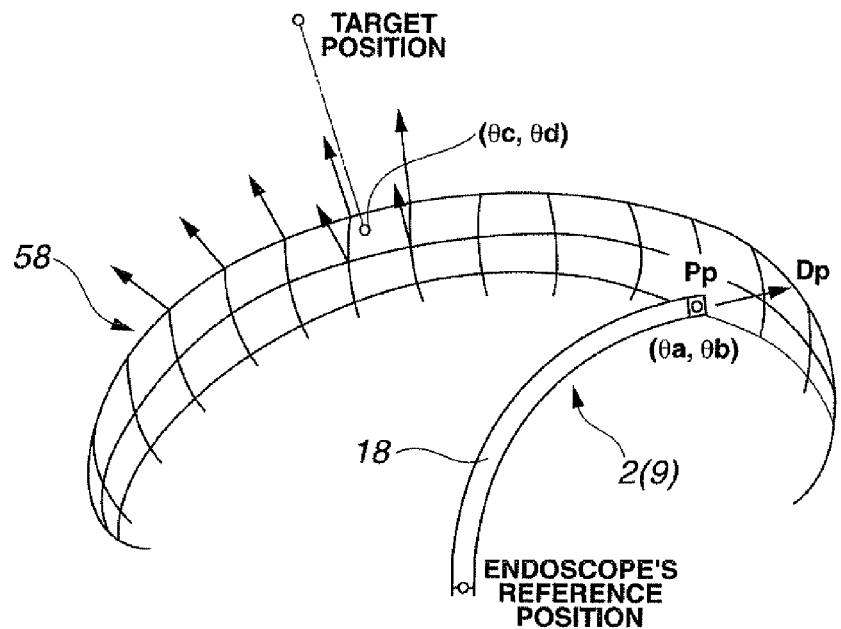
FIG. 17 is an explanatory diagram showing how to calculate target pulley angles used to bend the distal end of the endoseope from a current setting to a target position.
Figure 18:
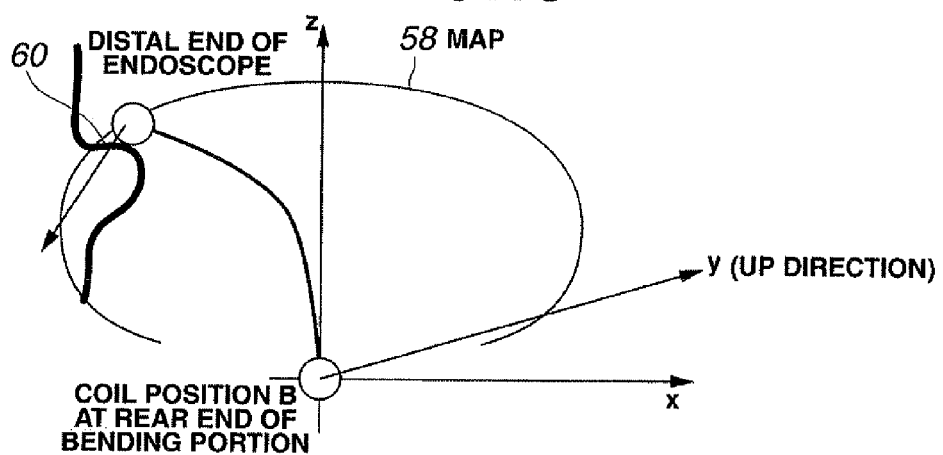
FIG. 18 is an explanatory diagram showing how a fold is held down by the distal end of the endoscope.

FIG. 15 illustrates how an Up direction of the distal end of the endoscope is made to coincide with a y-axis direction, FIG. 16 illustrates how a quaternion is used, FIG. 17 illustrates how to calculate target pulley angles used to bend the distal end of the endoscope from a current setting to a target position, FIG. 18 shows how a fold is held down by the distal end of the endoscope.

As shown in FIG. 1, an endoscope system 1 according to a first embodiment of the present invention includes an endoscope apparatus 6 which in turn includes an endoscope 2 used for endoscopy, light source device 3, processor 4, and endoscope monitor 5; a personal computer proper (hereinafter abbreviated to a PC proper) 7 which performs image processing of endoscopic images picked up by the endoscope 2 and bending control; a PC monitor 8; and a UPD apparatus 11 serving as means for endoscope shape detection including position detection at least on a distal side of an insertion portion 9 of the endoscope 2.

As shown in FIG. 1, the endoscope 2 has the elongated insertion portion 9 and inserted into a body cavity (lumen) of a patient 13, i.e., a subject, lying on a bed 12, and an operation portion 14 installed at a rear end of the insertion portion 9. A connector at an end of a universal cable 15 extending from the operation portion 14 is connected to the light source device 3 which generates illuminating light as well as to the processor 4 serving as a signal processing unit which performs signal processing.

As shown in FIG. 2, the insertion portion 9 includes a distal end portion 10 installed at a distal end of the insertion portion 9, a bending portion 18 configured to be bendable and installed at a rear end of the distal end portion 10, and a flexible portion 19 configured to be flexible and extending from a rear end of the bending portion 18 to an operation portion 14.

The operation portion 14 contains, for example, a joystick 21 serving as bend command input means used to give a command to bend the bending portion 18 in a direction desired by an operator 20. By operating the joystick 21 the operator 20 can electrically bend the bending portion 18 via a motor unit 22 installed in the operation portion 14 and serving as electrical bending drive means.

When the operator 20 selects an automatic bending control mode (described later), the PC proper 7 performs motor control for electrical bending control of the bending portion 18 via the motor unit 22 so that the distal side of the insertion portion 9 will turn to a running direction of a lumen through which the insertion portion 9 is passed.

Also, as shown in FIG. 1, an amount-of-twist detecting unit is installed, for example, on an outer periphery of the rear side of the insertion portion 9 to enable detecting an amount of twist (amount of rotation) when the insertion portion 9 is twisted around its axis.

The endoscope apparatus 6 shown in FIG. 1 has an appearance such as shown in FIG. 2. In FIG. 2, the PC proper 7 constitutes a component of the endoscope apparatus 6 as a control unit for the motor unit 22 in the endoscope 2.

Although the joystick 21 is used for the endoscope 2 in FIG. 1, a joypad may be used as bend command input means, as shown in FIG. 2.

In addition to a regular bending control mode in which the operator 20 inserts the endoscope 2 by manually operating the joystick 21 serving as bend command input means with the distal end portion 10 turned in the running direction of a lumens the endoscope system according to the present embodiment has an automatic bending control mode which involves estimating three-dimensionally a position of a dark part in a lumen (as a target position) from endoscopic images through image processing, estimating an insertion shape on the distal side of the insertion portion 9, and thereby controlling electrically bending of the bending portion 18 so that the distal end of the insertion portion will turn to the target position. Incidentally, the term "distal end of the insertion portion" and the term "distal end of the endoscope" are used interchangeably herein.

As shown in FIG. 3, a light guide 31 which transmits illuminating light is passed through the insertion portion 9. A rear end of the light guide 31 is connected to the light source device 3 via the operation portion 14 and universal cable 15 shown in FIG. 1 or FIG. 2.

Illuminating light from a lamp (not shown) in the light source device 3 is incident upon a rear end face of the light guide 31. Then, the illuminating light transmitted by the light guide 31 is emitted forward from a light guide's front end face fixed to an illuminating window in the distal end portion 10.

The illuminating light emitted forward through the illuminating window along a longitudinal axis of the insertion portion 9 illuminates an area ahead along a longitudinal axis of the body cavity in which the insertion portion 9 is inserted. As shown in FIG. 3, an objective lens 32 which forms an optical image is mounted in an observation window installed adjacent to the illuminating window, and its observation field of view or range of image pickup is illuminated by the illuminating light.

The objective lens 32 which forms an optical image and, for example, a CCD 33 placed as a solid-state image pickup element at an image focus location are included in an image pickup apparatus 34 serving as image pickup means.

A CCD output signal or image pickup signal photoelectrically converted by the CCD 33 is inputted in the processor 4. The processor 4 performs signal processing of the image pickup signal, and thereby generates, for example, an RGB signal and the like as an endoscopic image signal (video signal) used to display an endoscopic image on the endoscope monitor 5. The endoscopic image signal is inputted in the endoscope monitor 5, and consequently the endoscopic image is displayed in an endoscopic image display area of the endoscope monitor 5.

The endoscopic image signal is also inputted in the PC proper 7 serving as an image processing/motor control apparatus which performs image processing and motor control (or bending control). The endoscopic image signal is used there for image processing to detect position information needed to insert the distal end of the insertion portion 9 along the running direction of the body cavity.

Also, in the insertion portion 9 of the endoscope 2 according to the present embodiment, to detect insertion shape (also referred to as endoscope shape) of the insertion portion 9, multiple UPD coils (hereinafter simply referred to as coils) 36a, 36b, 36c, 36d, . . . serving as position information generating means which generates respective position information are arranged, for example, at predetermined intervals from the distal end portion 10 to an appropriate position in the flexible portion 19.

The coils 36a, 36b, 36c, 36d, . . . are, for example, magnetic field generating coils which generate magnetic fields. By detecting coil positions of the coils 36a, 36b, 36c, 36d, . . . , it is possible to calculate the insertion shape of the insertion portion 9.

In particular, by detecting the positions of multiple coils, for example, 36a and 36b in a distal end portion of the insertion portion 9, it is possible to detect not only distal end position of the insertion portion 9, but also an axial direction of the insertion portion 9 as the insertion shape. In the example of FIG. 3, the coil 36c is placed in the bending portion 18 and the coil 36d is placed at the rear end of the bending portion 18.

In this way, by detecting the positions of the coils 36a, 36b, 36c, 36d, . . . arranged on a distal side of the insertion portion 9, it is possible to detect bent shape of the distal end portion 10 and the bending portion 18. Incidentally, coil arrangement is not limited to the example shown in FIG. 3.

According the present embodiment, using position of the rear end of the bending portion 18 (position of the coil 36d, in the example of FIG. 3) as a reference (coordinate) position (as described later), a map is generated to associate driving positions (specifically, rotational drive angles and pulley angles) of the bending drive means and three-dimensional positions of the distal end of the insertion portion 9 with each other by bending the bending portion 18 in all directions in which the bending portion 18 is bendable-up and down and left-and-right.

Using the map information and based on a current position and direction of the distal end of the insertion portion 9, the present embodiment makes it possible to perform control accurately in a short time so as to turn the distal side of the insertion portion 9 into a direction of the target position, such as a dark part, to which the operator wants to bend the bending portion 18.

FIG. 4 shows the distal side of the insertion portion 9 in enlarged form. The coils 36a, 36b, 36c, 36d, . . . are arranged on the distal side of the insertion portion 9.

As shown in FIG. 4, in addition to the coils 36a, 36b, 36c, and 36d arranged along the longitudinal axis, a coil 36a' orthogonal, for example, to the coil 36a placed on the longitudinal axis is placed adjacent to the coil 36a in the distal end portion 10 with a solenoid axis (axis of an winding) of the coil 36a' turned into an upward bending direction (referred to as the Up bending direction or simply as the Up direction) when the bending portion 18 is bent.

In this case, windings of the coil 36a and coil 36a' are orthogonal to each other. However, this is not restrictive, and the windings of the coil 36a and coil 36a' may be placed parallel to each other.

With this arrangement, by detecting the positions of the coils 36a, 36b, 36c, 36d, 36a', . . . , it is possible to detect (estimate) not only the position and axial direction of the distal end portion 10, but also a direction around an axis of the distal end portion 10 (the Up direction, and an upward direction of the CCD 33) as insertion shape of the endoscope.

In this way, by detecting insertion shape on a distal side of the endoscope including information about the bending direction of the distal side of the endoscope using coil position detecting means, it is possible to detect (estimate) bent condition of the bending portion 18 with the endoscope inserted. This makes it easy to perform bending control of the bending portion 18 so as to turn the distal side of the endoscope in the direction of the target position such as a dark part.

A cable on a rear side of the coils 36a, 36b, 36c, 36d, . . . is connected to the UPD apparatus 11.

The UPD apparatus 11 shown in FIG. 1 includes a UPD drive circuit (not shown) and sense coil unit 11a, where the UPD drive circuit generates magnetic fields by applying a drive signal of a predetermined frequency to the coils 36a, 36b, 36c, . . . and the sense coil unit 1a is made up of multiple sense coils arranged in a predetermined positional relationship to detect magnetic fields.

Also, the UPD apparatus 11 includes a position detecting unit 11b (see FIG. 2) which detects (calculates) positions of the coils 36a, 36b, 36c, . . . based on detection signals from the multiple sense coils, an insertion shape calculation/display processing circuit 11c which calculates the insertion shape of the insertion portion 9 (endoscope 2) based on position information about the coils 36a, 36b, 36c, . . . and performs display processing of the calculated insertion shape, and a shape display monitor 11d which displays the insertion shape.

Incidentally, at least the sense coil unit 11a in the UPD apparatus 11 is placed near the bed 12 shown in FIG. 1 to detect three-dimensional coordinate positions of the coils 36a, 36b, 36c, . . . in a world coordinate system, i.e., in a coordinate system which covers a three-dimensional domain where the insertion portion 9 is inserted in the patient 13 lying on the bed 12.

An amount-of-twist detecting unit 23 which detects the amount of twist of the insertion portion 9 as shown in FIG. 1 is not strictly necessary if a specific bearing (e.g., the Up direction) of the distal end portion 10 can be detected by the coil 36a' shown in FIG. 3.

FIG. 5 shows an example of insertion shape generated by the UPD apparatus 11. As shown in FIG. 5, in the three-dimensional coordinate system, the positions (Xji, Yji, Zji) (where i=a, b, . . . , m) of the coils 36a, 36b, 36c, . . . in j frames (where j=0, 1, 2, . . . ) are calculated, and the insertion shape is generated by joining the calculated positions.

Data on the insertion shape including the positions of the coils 36a, 36b, 36c, 36d, . . . detected by the UPD apparatus 11 is configured as frame data on the individual frames (i.e., 0th frame data, 1st frame data, . . . ) as shown in FIG. 6A, and transmitted in sequence to the PC proper 7.

The frame data of each frame serving as insertion state information includes creation time of the insertion shape data, display properties, supplementary information, three-dimensional coordinate data of the coil (coil coordinate data), and the like as shown in FIG. 6B.

The coil coordinate data represents three-dimensional coordinates of the coils 36a, 36b, 36c, 36d, . . . arranged in sequence from distal side to proximal side (nearer to the operation portion 14) of the insertion portion 9 as shown in FIG. 6C.

On the other hand, endoscopic images obtained by the image pickup apparatus 34 installed in the distal end portion 10 vary with the amount of insertion of the insertion portion 9 into a body cavity (lumen such as the large intestine).

Consequently, position information about a dark part in the lumen (also referred to as a luminal dark part) detected in the endoscopic images is transformed into the world coordinate system. The position information about the dark part corresponds to the running direction of the lumen, and thus the position information provides a target position in an insertion direction along which the distal end of the insertion portion is inserted (introduced) deeper into the lumen, that is, a target position in the bending direction.

Incidentally, the endoscope 2 is of a direct view type, meaning that an observation direction (image pickup direction) via the image pickup apparatus 34 installed in the distal end portion 10 is parallel to the longitudinal axis of the insertion portion 9. Also, the observation direction via the image pickup apparatus 34 coincides with the insertion direction.

The information about coil coordinate positions and coil directions of the coils 36a, 36b, 36c, 36d, . . . detected by a coil position detecting unit in the UPD apparatus 11 is also inputted in the PC proper 7 (see FIG. 7 described later).

As shown schematically in FIG. 3, the bending portion 18 is made up of multiple bending pieces rotatably coupled in a longitudinal direction of the bending portion 18. Also, bending wires 41u, 41d, 41l, and 41r are passed through the insertion portion 9 along up, down, left, and right bending directions. Rear ends of the bending wires 41u, 41d, 41l and 41r are coupled, for example, to pulleys 42a and 42b of the motor unit 22 in the operation portion 14.

In the operation portion 14, the up and down bending wires 41u and 41d which are joined end to end are looped around the pulley 42a while the left and right bending wires 41l and 41r which are joined end to end are looped around the pulley 42b.

The pulleys 42a and 42b are coupled, respectively, to rotation axes of an UD motor 43a for up and down bending (driving) and Rn motor 43b for left and right bending (which may be referred to simply as motors 43a and 43b) and rotated according to rotational directions of the motors 43a and 43b which can rotate in forward and reverse directions. The motors 43a and 43b serving as up-and-down and left-and-right bending drive means are controlled by the PC proper 7 connected with the motor unit 22 as shown in FIG. 7.

This configuration provides electrical bending drive means which rotates the pulleys 42a and 42b using the motors 43a and 43b to pull and relax (push-pull) the bending wires 41u, 41d, 41l, and 41r, and thereby electrically drives and bends the bending portion 18.

An amount of bending of the bending portion changes with amounts of rotation by which the pulleys 42a and 42b are rotated by the motors 43a and 43b, and the amounts of rotation of the pulleys 42a and 42b are referred to as pulley angles.

Rotation angles of the motors 43a and 43b (also referred to as motor angles) or the pulley angles are detected respectively, for example, by an up/down rotary encoder (UD encoder) 44a and left/right rotary encoder (RL encoder 44b) mounted on the respective rotation axes of the motors 43a and 43b and serving as rotation angle detecting means or rotational position detecting means. Encoder outputs from the UD encoder 44a and RL encoder 44b are inputted in the PC proper 7 as shown in FIG. 7.

In the automatic bending control mode, the motors 43a and 43b in the motor unit 22 controls electrically-driven bending using map information (described later) and based on the target position estimated by the UPD apparatus 11 and received from the PC proper 7 and the current position and direction of the distal end portion 10 (of the endoscope). Thus, the PC proper 7 has a function of bending control means.

Besides, the PC proper 7 calculates the target position through image processing (described later) to determine the target direction of bending.

In the case of manual bending, when the operator moves the joystick 21 installed in the operation portion 14 and serving as bend command input means in a desired bending direction out of the up, down, left, and right directions, the PC proper 7 controls amounts of rotational driving of the motors 43a and 43b (which correspond to the pulley angles of the pulleys 42a and 42b) so as to bring the encoder outputs into coincidence with the amount of operation of the joystick 21 and thereby bends the bending portion 18 by the specified amount of bending.

For that, the joystick 21 is equipped, for example, with an encoder or potentiometer (not shown) to detect amounts of tilting operations in an up-and-down direction and left-and-right direction. The encoder or potentiometer finds specified amount of bending and information about a specified direction. In this case, the PC proper 7 performs bending control so as to simply bring the encoder outputs into coincidence with the specified amount of bending.

FIG. 7 shows a functional configuration of the PC proper 7. An endoscopic image signal from the processor 4 is stored as endoscopic image data in a memory 52 via an A/D converter circuit 51 in the PC proper 7.

Information about coil coordinates and directions supplied from the UPD apparatus 11 is stored in the memory 52 via a coil information acquisition thread 53 as endoscope shape parameters, specifically, as data on coil coordinate positions, coil directions, and the distal end's Up direction.

The endoscopic image data and endoscope shape parameter data are outputted to a main processing unit (or main thread) 55 formed by a CPU.

Incidentally, the CPU may be configured to perform not only processes of the main processing unit 55, but also other processes such as processes of an amount-of-bending control thread 56 described later. Alternatively, the main processing unit 55 in FIG. 7 may be configured to perform the processes of the amount-of-bending control thread 56.

The encoder outputs from the motor unit 22 of the endoscope 2 are inputted in the amount-of-bending control thread 56 which also accepts input of amount-of-bending parameter data generated by the main processing unit 55 and stored temporarily in the memory 52.

The amount-of-bending parameters include additional pulley angles by which the pulley needs to be moved from the current pulley angles in a direction of the target position. The additional pulley angles are relative pulley angles given, for example, in the form of differential values (described later).

Incidentally, as shown in a dotted box in FIG. 7, when the amount-of-twist detecting unit 23 is used, the relative amount of twist detected by the amount-of-twist detecting unit 23 is stored, for example, as one of the endoscope shape parameters in the memory 52 via an amount-of-twist acquisition thread 57.

According the present embodiment, the memory 52 also stores information of a data map (lookup table) 58 obtained by measuring and digitizing a relationship between pulley angle positions and three-dimensional positions and directions of the endoscope's distal end, where the pulley angle positions which are handled by the bending drive means correspond to the amount of bending (including bending directions) produced when the bending portion 18 is bent up and down or left and right. Thus, the memory 52 serves as map information storage means.

Motor angles which are rotation angles of the motors 43a and 43b may be used instead of the pulley angles. Alternatively, gear angles which are rotation angles of gears may be used if the pulleys 42a and 42b are rotationally driven via gears coupled to the rotation axes of the motors 43a and 43b.

In that case, when the map 58 is generated, a reference (coordinate) position is established at such a position of the insertion portion 9 that is located near the distal end of the insertion portion 9 and hardly affected when the bending portion 18 is bent. Specifically, the reference position is established at the rear end of the bending portion 18.

Consequently, data of the map 58 (the data is also referred to as map information) can be used commonly in any bent condition (condition of the pulley angles), provided that the same endoscope 2 is used.

Incidentally, according to the present embodiment, the map information accommodates cases in which a bendable range of the bending portion 18 (i.e., maximum pulley angle) varies among different directions, such as between up-and-down direction and left-and-right direction or between up and down directions. Also, the map information accommodates bending not only in four directions of up, down, left, and right, but also in any intermediate direction, such as direction between up and left directions.

Also, data of the map information is generated using a predetermined bending direction as a reference direction. According to the present embodiment, for example, the map information is generated with bending in the up direction (U or Up) represented by a y axis on the map 58 (described later).

When the distal end of the endoscope is bent (or oriented) in the intended direction using the map information, the coordinate system and target direction of the endoscope's distal end are matched to the coordinate system of the map information.

Also, as described with reference to FIG. 8, using the map information and based on the current shape information about the distal end of the endoscope, the main processing unit 55 calculates the pulley angles to bend the bending portion 18 in the direction of the target position and sends the calculated pulley angles to the amount-of-bending control thread 56 via the memory 52.

The amount-of-bending control thread 56 converts the calculated pulley angles into motor voltages (more specifically, a UD motor voltage value and RL motor voltage value) and outputs the motor voltages to the UD motor 43a and RL motor 43b in the motor unit 22.

FIG. 8 shows a functional configuration of the main processing unit 55.

As shown in FIG. 8, the main processing unit 55 has functions of an intra-image target position detecting section 55a which detects the target position based on lumen information in an endoscopic image, an endoscope shape processing section 55b which detects the positions and directions of various parts of the endoscope using coil coordinates, and an amount-of-twist calculating section 55c which calculates an absolute amount of twist from a relative amount of twist. The endoscope shape processing section 55b has a function of position and direction detecting means which detects the position and direction of the endoscope's distal end.

Incidentally, as shown in a dotted box, the amount-of-twist calculating section 55c performs its process when a relative amount of twist is inputted.

The intra-image target position detecting section 55a detects a center position (or center of gravity position) of a dark part which corresponds to the running direction of the lumen in an endoscopic image, where the center position of the dark part is detected in the endoscopic image as two-dimensional position information.

The position of the dark part is detected by taking into consideration pixel size, focal length, and other values of the CCD 33. Then, based on information about the position of the dark part in relation to the current distal end position of the insertion portion 9, the direction of the position of the dark part is detected as the insertion direction of the insertion portion's distal end (endoscope's distal end).

In addition to the two-dimensional position information about the dark part, a three-dimensional position including a value in a depth dimension of the dark part is calculated, for example, by SFS-based image processing, where SFS stands for Shape From Shading which is a technique for shape recovery from shading. The three-dimensional position information is used as a target position to which the distal end of the insertion portion should be introduced (oriented).

The target position detected by the intra-image target position detecting section 55a is transformed into a target position in the world coordinate system by a coordinate system transformation unit of the intra-image target position detecting section 55a. The direction of the resulting target position corresponds to the target direction in which the distal end of the insertion portion should be inserted.

The resulting target position is outputted to an amount-of-bending calculating section (pulley angle calculating portion) 55d which calculates the amount of bending or pulley angles.

Information about the positions and directions of various parts of the endoscope is inputted in the amount-of-bending calculating section 55d from the endoscope shape processing section 55b.

Also, the absolute amount of twist is inputted in the amount-of-bending calculating section 55d from the amount-of-twist calculating section 55c The absolute amount of twist is not calculated if the amount-of-twist detecting unit 23 is not installed.

The rotation angle by which the insertion portion 9 is rotated around its axis is detected based on the amount of twist detected by the amount-of-twist detecting unit 23. Incidentally, even if the amount-of-twist detecting unit 23 is not installed, the bending direction of the endoscope's distal end can be calculated by detecting the positions of the coils 36a and 36a' shown in FIG. 4 (without using the amount of twist because the Up direction can be detected).

The amount-of-bending calculating section 55d calculates the current bent condition of the endoscope's distal end from information about the position and direction of the endoscope's distal end out of inputted information with reference to the map information.

After calculating the current bent condition, the amount-of-bending calculating section 55*d* calculates the pulley angles used to bend the distal end of the endoscope from the current bent condition toward the target position, with reference to the map information.

That is, using the map information, the amount-of-bending calculating section 55*d* serves as calculating means for calculating the current position and direction of the endoscope's distal end and calculating means for calculating the direction of the target position.

The calculated pulley angles are outputted as additional pulley angles to the amount-of-bending control thread 56 via the memory 52. The amount-of-bending control thread 56 converts the additional pulley angles into motor voltages (UD motor voltage value and RL motor voltage) and applies the motor voltages to the UD motor 43*a* and RL motor 43*b* in the motor unit 22.

As the UD motor 43*a* and RL motor 43*b* are driven rotationally, the bending portion 18 is bent so as to bring the distal end of the endoscope into coincidence with the direction of the target position.

Next, the process of creating the map 58 used for bending control will be described with reference to FIG. 9. Incidentally, the map 58 is created before the endoscope is shipped, for example, from the factory.

As shown in FIG. 9, in Step S1, a map creator sets the pulley angles ($\theta 1$, $\theta 2$) in the up-and-down and left-and-right directions using the pulley angle $\theta 1$ in the up-and-down direction and pulley angle $\theta 2$ in the left-and-right direction.

In FIG. 10, to carry out Step S1 concretely, representative pulley angle values are specified as positions on the map. FIG. 10 shows an example of the map used in Step S1. The map is made, for example, of a tetragonal lattice (grid). When the process in FIG. 9 is finished, the map 58 is completed.

In FIG. 10, with an origin at (0, 0), the pulley angle $\theta 1$ in the up-and-down direction (denoted by Up and D) and pulley angle $\theta 2$ in the left-and-right direction (denoted by L and R) can be specified within a range of bending characteristics of the endoscope 2 used actually.

For example, in FIG. 10, actually available pulley angle ranges are from $\theta Dm$ to $\theta Um$ for the pulley angle $\theta 1$ in the up-and-down direction, and from $\theta Lm$ to $\theta Rm$ for the pulley angle $\theta 2$ in the left-and-right direction. In this case, $\theta Dm$ and $\theta Lm$ are defined as negative values. Also, according to the present embodiment, the upward direction (Up direction) is represented by the y axis as a reference direction of the map 58, as shown in FIG. 10.

In Step S1 ($\theta 1i$, $\theta 2j$), for example, are actually set as the pulley angles ($\theta 1$, $\theta 2$), where i and j represent the pulley angles on the grid. A display example is shown in FIG. 10.

Incidentally, a grid offset value $\Delta\theta$ of the pulley angle values is used in the flowchart (Step S4).

By maintaining the pulley angles ($\theta 1i$, $\theta 2j$) set in Step S1, the map creator measures coordinates and directions of the endoscope's reference position and distal end position in Step S2.

FIG. 11 shows an example of the endoscope's reference position coordinates ($X_0$, $Y_0$, $Z_0$), endoscope's distal end position coordinates (Xij,Yij, Zij), and directions $D_0$ and Dij at the given positions, measured in Step S2 with the pulley angles ($\theta 1i$, $\theta 2j$) maintained. Incidentally, in this case, for example, the direction $D_0$ contains information about the axial direction at the endoscope's reference position with reference to a specific direction of bending (specifically, the up direction of bending).

In Step S3, three-dimensional relative coordinates and a relative direction of the endoscope's distal end with respect to the coordinates and direction of the endoscope's reference position are calculated and written to appropriate map positions.

Specifically, the relative coordinates (Xii–$X_0$,Yij–$Y_0$, Zij–$Z_0$) and relative direction (Dij–$D_0$) of the endoscope's distal end position are written to the position (map position or map data position) at a grid point for the pulley angles ($\theta 1i$, $\theta 2j$) in FIG. 10, by being associated with each other.

Although a single set of pulley angles ($\theta 1i$, $\theta 2j$) has been described concretely, association is established similarly at other pulley angle values using the offset value $\Delta\theta$ in a subsequent step.

That is, with the endoscope's reference position in FIG. 11 set as the origin and the direction at the origin set to 0, the values of the position coordinates and direction of the endoscopers distal end are written to each map data position by being associated with each set of pulley angles ($\theta 1i$, $\theta 2j$). In other words, the values of the relative position coordinates and relative direction with respect to the endoscope's reference position are associated with the pulley angles.

In Step S4, the map creator adds the offset value $\Delta\theta$ to the pulley angles $\theta 1$ and $\theta 2$ to obtain pulley angles $\theta 1$ and $\theta 2$ at an adjacent grid position.

In Step S5, the map creator determines whether the pulley angles $\theta 1$ and $\theta 2$ have exceeded the ranges of the pulley angles for the endoscope. If the ranges are not exceeded, the map creator returns to Step S1 and repeats processes of Steps S1 to S5. Actually, the processes of Steps S1 to S5 are repeated within the ranges of the pulley angles in the up-and-down direction and left-and-right direction as long as the bending portion 18 can be bent.

The map 58 is created in this way. The map 58 stores pulley angles ($\theta 1i$, $\theta 2j$) at each map position in FIG. 10 by associating the corresponding relative coordinates (Xij–$X_0$,Yij–$Y_0$, Zij–$Z_0$) and relative direction (Dij–$D_0$) of the endoscope's distal end.

When each data item in the map 58 is expressed in a three-dimensional coordinate system representing the endoscope's distal end, the map 58 presents a curved surface which represents a locus obtained by plotting the endoscope's distal end position in the three-dimensional coordinate system in the case where a bending portion 18 is bent.

Also, the axial direction of the distal end at the endoscope's distal end position is digitized as direction information together with the position.

Thus, on the map 58, by specifying the current position of the endoscope's distal end, it is possible to calculate the corresponding current direction of the endoscope's distal end.

Incidentally, the procedures for creating the map 58 in FIG. 9 may be automated.

When the map 58 is expressed as a curved surface, the map 58 as viewed in the U direction from the D direction of the endoscope's distal end (side view of the map) and the map 58 as viewed in the L direction from the R direction of the endoscope's distal end (side view of the map) are shown in FIGS. 12A and 12B, respectively.

Incidentally, in FIGS. 12A and 12B, a line segment which represents the direction of the endoscope's distal end is shown three-dimensionally. Part of the map 58 viewed from a direction different from the directions in FIGS. 12A and 12B is schematically shown by way of example in FIG. 17. In FIG.

17, a line segment which represents the direction of the endoscope's distal end in FIGS. 12A and 122B is shown vectorially by attaching an arrow to an end of the line segment.

Although it has been stated that the map 58 is created before shipment from the factory, this is not restrictive, and a program for creating a map 58 may be stored in the PC proper 7 so that the PC proper 7 will create a map 58 according to the program. Alternatively, a program for creating a map 58 may be transferred to the endoscope system 1 which does not have a map 58, allowing the endoscope system 1 to create a map 58. In this way, the endoscope system I may be provided with means of creating a map 58.

Next, operation of bending control performed by the main processing unit 55 using the map information (generated as described above) in the present embodiment will be described with reference to FIG. 13.

First, initialization is performed in Step S11. Next, in Step S12, the main processing unit 55 acquires coil information about the coils 36a, 36b, 36c . . . arranged in the insertion portion 9, i.e., information about coil positions.

In Step S13, the CPU functioning as the main processing unit 55 calculates the position and direction of the endoscope's distal end based on the information about coil positions. In Step S14, the CPU acquires image data of an endoscopic image.

In Step S15, the CPU corrects distortion in image data. Specifically, the CPU corrects distortion in image data obtained by the objective lens 32, which is prone to distortion aberrations.

In Step S16, using the endoscopic image, the CPU detects a target position to pass through the distal end of the endoscope. Specifically, the CPU detects the position of a luminal dark part.

In Step S17, the CPU transforms the target position detected in Step S16, which is two-dimensional position information, into three-dimensional coordinates using the SFS technique or the like.

In Step S18, using the map information, the CPU calculates target pulley angles (described later with reference to FIG. 14) which correspond to the bending direction to bring the direction of the endoscope's distal end into coincidence with the direction of the target position (or orient the distal end in the direction of the target position).

In Step S19, the CPU calculates motor voltages corresponding to the calculated target pulley angles. The calculation is performed as a process of the amount-of-bending control thread 56 in the exemplary configuration shown in FIG. 7. The calculated motor voltages are applied to the motors 43a and 43b in the motor unit 22 to electrically drive and bend the bending portion 18 through rotation of the motors 43a and 43b.

Next, the process of calculating the target pulley angles will be described with reference to FIG. 14.

First, in Step S21, the CPU functioning as the main processing unit 55 transforms the coordinates of the target position into relative coordinates defined with respect to the endoscope's reference position.

Next, in Step S22, the CPU performs a transformation such that the Up direction on the distal side of the endoscope will coincide with the y axis and that the axial direction of a coil position B will coincide with the Z axis. This constitutes transformation conditions or setting conditions for a match to a coordinate system of the map 58 which is to be used. This can be understood readily from the process used to create the map 58.

FIG. 15 illustrates the process of Step S22. In Step S21, the distal side of the endoscope is generally in a state shown in FIG. 15. Incidentally, the coil position B coincides with a reference position at the rear end of the bending portion as shown in FIG. 15.

As shown in FIG. 15, a position A of the endoseope's distal end (represented concretely by a coil at the distal end) is located on the map 58 (the curved surface of the map), and generally the Up direction of the endoscope in this state does not coincide with the Up direction of the map 58.

Therefore, a rotational transform is performed such that the Up direction of the endoscope will coincide with a reference direction (for example, the y axis) predefined as the Up direction of the map 58. As a result of the transform, the target position also moves as indicated by an arrow in FIG. 15. The rotation can be performed easily using a quaternion.

A C axis orthogonal to the Up direction of the endoscope's distal end and the y axis of the map 58 in FIG. 15 is defined as shown in FIG. 16. Then, the Up direction of the endoscope's distal end and the y-axis direction of the map 58 are brought into coincidence with each other by rotating them around the C axis by a rotation angle $\phi$.

As shown in FIG. 16, the rotation by the rotation angle $\phi$ moves the coil position A at the distal end to a position denoted by reference numeral B'. A quaternion generated using a direction vector, which defines the C axis, and the rotation angle $\phi$ makes it easy to transform the coil position A at the distal end. A similar transformation is performed so as to bring the axial direction of the resulting coil position B' into coincidence with the Z axis.

After the process of Step S22 in FIG. 14, the CPU calculates position coordinates (e.g., consecutive coordinates) on the map coordinate system corresponding to the direction of the target position in Step S23.

Specifically, the CPU identifies a position (position and direction of the endoscope's distal end) on the map which best approximates the direction of the target position. The process of Step S23 belongs to the direction-of-the-target-position calculating unit.

After calculating a map position which approximates the direction of the target position in Steps S21 to S23, the CPU similarly processes the current distal end of the endoscope in Steps S24 to S26 to calculate the corresponding position on the map.

Specifically, in Step S24, the CPU transforms the coordinates of the endoscope's distal end into relative coordinates defined with respect to the endoscope's reference position. Next, in Step S25, the CPU performs a transformation such that the Up direction of the endoscope will coincide with the y axis and that the axial direction of the coil position B will coincide with the Z axis.

In Step S26, the CPU calculates position coordinates (e.g., consecutive coordinates) on the map coordinate system corresponding to the position of the endoscope's distal end. Step S26 makes it possible to calculate the direction in which the current position of the endoscope's distal end should be oriented. Step S26 belongs to the direction-of-the-distal-end calculating unit.

In Step S27, the CPU calculates values of the target pulley angles based on the map coordinates.

FIG. 17 shows how the target pulley angles are calculated in Step S27. As shown, for example, in FIG. 17, using the current distal end of the endoseope (coordinates Pp, direction Dp) identified in Step S26, corresponding pulley angles ($\theta a$, $\theta b$) are calculated as current absolute pulley angle values.

Also, in Step S23, target position pulley angles ($\theta c$, $\theta d$) corresponding to the target position are calculated as absolute pulley angle values.

Differential values between the absolute pulley angle values, i.e., relative pulley angles (θc−θa, θd−θb), are calculated as target pulley angles. The target pulley angles are set as a bending control target (shown in Step S18 in FIG. 13) and used for bending control in moving the distal end of the endoscope from the current position to the target position.

As can be seen from the process in Step S27, to bend the distal end of the endoscope from the current state (generally a bent state) toward the target position, the amount of bending (driving) is determined from the differential values (i.e., relative values) between the pulley angles (θa, θb) corresponding to the current bent condition and the pulley angles (θc, θd) corresponding to the target position.

Therefore, even if the bending wire is extended due to repeated bending operations or aging, causing misalignment (displacement of the reference position) which involves a discrepancy between the amount of bending operation on the hand side and the amount of bending on the distal side, the use of relative values in determining the amount of electrically-driven bending enables accurate bending control.

As a further note, for bending from the current position and direction of the endoscope's distal end toward a target position of bending, for example, the pulley angle values corresponding to the current position and direction of the endoscope's distal end on the map 58 are used instead of the actual pulley angle values on the hand side.

Consequently, the use of relative values calculated from the map 58 enables accurate bending control even if the bending wire is extended, causing deviations in reference values which are based on the actual pulley angles on the hand side.

Also, according to the present embodiment, three-dimensional bending information about the bending portion 18 has been gathered by bending the bending portion 18 and digitized as the map 58. Although it is possible to perform bending control by carrying out arithmetic operations and the like without using the map 58, the present embodiment makes it possible to perform bending control using simpler arithmetic operations.

Also, since the use of the map 58 allows the direction and amount of bending to be calculated in a shorter time than when the map 58 is not used, the present embodiment enables highly responsive bending control.

That is, the (data) map 58 is generated by digitizing the coordinate values of a large number of pulley angles produced by bending the bending portion 18 finely in the up, down, left, and right directions and three-dimensional position and direction of the endoscope's distal end corresponding to the coordinate values of each pulley angle.

Consequently, if one of the coordinate values and the three-dimensional positions and directions is known, the other can be read out easily. That is, the direction and amount of bending can be calculated easily in a short time without the need for complicated arithmetic operations.

Also, when it becomes necessary to calculate directions and amounts of bending corresponding to values unavailable in the map 58, which contains discrete values, desired values can be calculated easily from available values close to the desired values using, for example, the Pseudo-Newton method which is an approximation method (approximate estimation method).

For example, as shown in FIG. 17, it is necessary to calculate the target position's pulley angles (θc, θd) corresponding to the direction of the target position on the coordinate system of the map 58 using the coordinates of the target position. In this case, since the position and pulley angle values at each grid point are known, amounts of deviation from the direction of the target position are determined at multiple grid points.

Then, values of a direction which reduces the three-dimensional amounts of deviation to sufficiently small values are calculated as approximate values using the Pseudo-Newton method, making it possible to calculate the target position's pulley angles (θc, θd) corresponding to the calculated direction.

In this way, using the map information which is three-dimensional information about bending information produced by bending the bending portion 18 on the distal side of the insertion portion 9, the present embodiment enables accurate bending control.

Also, as shown in FIG. 18, the present embodiment makes it easy to carry out a maneuver such as holding down a fold of the intestinal tract by the distal end of the endoscope.

That is, since the position and direction of the endoscope's distal end can be detected using the map 58, the present embodiment makes it easy to carry out a maneuver such as holding down a fold 60 in the direction indicated by an arrow using the distal end of the endoscope (represented schematically by the coil at the distal end) as shown in FIG. 18.

If data is generated by reducing grid intervals in FIG. 10, target pulley angles and the like can be calculated using data on the grid (at data points of the map) almost without using interpolation or the like.

Also, when a target position is located on the coordinate system of the map 58 or under similar conditions, using positions on the map 58, the differential values between the pulley angle values at the current position of the endoscope's distal end and the pulley angle values at the position corresponding to the target position can be calculated as target pulley angles.

Also, pulley angles on the map 58 may be calculated based on position information about the target position instead of using direction information about the target position.

Figure 19:
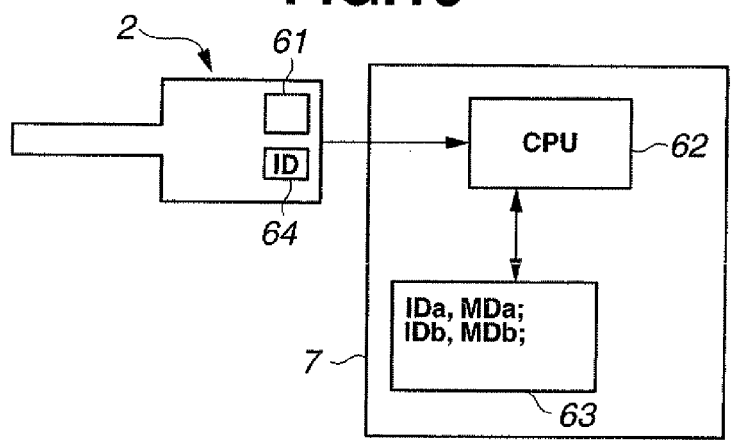
FIG. 19 is a block diagram showing a configuration of an endoscope and PC proper according to a variation of the present invention.

Incidentally, configuration shown in FIG. 19 may be used. FIG. 19 shows the endoscope 2 and PC proper 7 according a variation. As shown in the present variation, the endoscope 2 may incorporate a map information storage unit 61 (of a non-volatile memory or the like) containing information of the map 58 described above.

When the endoscope 2 is connected to the PC proper 7, a CPU 62 functioning as the main processing unit 55 and the like of the PC proper 7 may read information out of the map 58 and store the information on a hard disk 63, the non-volatile memory, or the memory 52 of the PC proper 7 in order to use the information in bending control.

After use, the information of the map 58 may be stored on the PC proper 7 by being associated with ID information possessed by the endoscope 2.

The endoscope 2 includes an ID information generating unit (abbreviated to ID in FIG. 19) 64 which generates ID information unique to the endoscope 2.

Incidentally, instead of being stored on the endoscope 2, the information of the map 58 for the endoscope may be stored on the PC proper 7 together with the ID information on the endoscope 2.

In the configuration shown in FIG. 19, ID information IDa is stored in pairs with map information MDa while ID information IDb is stored in pairs with map information MDb.

When the endoscope 2 is connected to the PC proper 7, the CPU 62 can read the ID information on the endoscope 2 and use the information of the map 58 corresponding to the ID information in bending control.

Even when different endoscopes 2 are connected to the PC proper 7, using the map information, i.e., three-dimensional bending information about the bending of the bending portion 18 of the currently connected endoscope 2, the present variation enables accurate bending control. In other respects, the present variation provides the same advantages as those of the first embodiment.

It should be noted that any embodiment obtained by combining some of the features of the above embodiment and the like is also included in the present invention.

What is claimed is:

1. An endoscope system comprising:
    an endoscope in which a bending portion configured to be bendable is installed on a distal side of an insertion portion;
    a bending drive unit which drives and bends the bending portion electrically;
    a map information storage unit which stores map information digitized by associating an amount of bending, including a bending direction, produced when the bending portion is bent and a three-dimensional position and direction of a distal end of the insertion portion corresponding to the amount of bending with each other, with a position near a rear end of the bending portion being designated as a reference position;
    a position and direction detecting unit which detects the three-dimensional position and direction of the distal end of the insertion portion; and
    a bending control unit which controls electrically-driven bending performed by the bending drive unit so as to orient the distal end of the insertion portion into a target direction using the map information, based on the three dimensional position and direction detected by the position and direction detecting unit.

2. The endoscope system according to claim 1, wherein the map information storage unit stores the map information digitized by associating a plurality of amounts of bending produced when the bending portion is bent in an up-and-down direction and a left-and-right direction by a plurality of different angles and three-dimensional positions and directions of the distal end of the insertion portion corresponding to the plurality of amounts of bending with each other, with the position near the rear end of the bending portion being designated as the reference position.

3. The endoscope system according to claim 1, wherein the amount of bending is represented by rotation angles of a plurality of motors or rotation angles of a plurality of pulleys rotated by the plurality of motors respectively, where the motors, being included in the bending drive unit, drive and bend the bending portion in different directions.

4. The endoscope system according to claim 1, further comprising a target direction calculating unit which calculates the target direction from an endoscopic image picked up by an image pickup unit installed at the distal end of the insertion portion of the endoscope.

5. The endoscope system according to claim 1, wherein the position and direction detecting unit detects the three-dimensional position and direction of the distal end of the insertion portion by detecting positions of a plurality of magnetic field generating coils arranged on the distal side of the insertion portion.

6. The endoscope system according to claim 1, wherein the bending control unit controls the bending drive unit so as to bend the bending portion by a relative angle corresponding to a differential value between values in two directions on a coordinate system of the map information, the two directions being the direction of the distal end of the insertion portion detected by the position and direction detecting unit and the target direction into which the distal end of the insertion portion is to be oriented.

7. The endoscope system according to claim 1, wherein the map information is stored in the map information storage unit by being associated with identification information about the endoscope.

8. The endoscope system according to claim 1, further comprising an amount-of-twist detecting unit which detects an amount of twist of the insertion portion around an axial direction of the insertion portion.

9. The endoscope system according to claim 1, further comprising a map creating unit which creates the map information.

10. The endoscope system according to claim 1, wherein the endoscope comprises the map information storage unit.

11. An endoscope system comprising:
    an endoscope which includes, on a distal end side, an insertion portion equipped with a bending portion configured to be bendable;
    a map information storage unit which stores map information digitized about a locus of a three-dimensional position and direction of a distal end of the insertion portion generated when the bending portion is bent, with a position near a rear end of the bending portion being designated as a reference position;
    a direction-of-the-distal-end calculating unit which calculates, on a coordinate system of the map information, a current direction of the distal end of the insertion portion using the map information when a current three-dimensional position of the distal end of the insertion portion is specified;
    a direction-of-the-target-position calculating unit which calculates, on a coordinate system of the map information, a direction of the target position into which the distal end of the insertion portion is to be oriented using the map information; and
    a bending control unit which bends the bending portion to move the distal end of the insertion portion from the current position toward the target position based on calculation results produced by the direction-of-the-distal-end calculating unit and the direction-of-the-target-position calculating unit.

12. The endoscope system according to claim 11, wherein the map information storage unit stores the map information digitized by associating a plurality of amounts of bending produced when the bending portion is bent in an up-and-down direction and a left-and-right direction by a plurality of different angles and three-dimensional positions and directions of the distal end of the insertion portion corresponding to the plurality of amounts of bending with each other, with the position near the rear end of the bending portion being designated as the reference position.

13. The endoscope system according to claim 12, further comprising a bending drive unit which drives and bends the bending portion electrically.

14. The endoscope system according to claim 13, wherein the amount of bending is represented by rotation angles of a plurality of motors or rotation angles of a plurality of pulleys rotated by the plurality of motors respectively, where the motors, being included in the bending drive unit, drive and bend the bending portion in different directions.

15. The endoscope system according to claim 11, wherein the direction-of-the-distal-end calculating unit transforms a current three-dimensional position and direction of the distal end of the insertion portion from a coordinate system in which the current three-dimensional position and direction have been detected into a relative coordinate system with an origin at the reference position and matches the current three-dimensional position and direction to a coordinate system of the map information before calculating a current direction of the distal end of the insertion portion on the coordinate system of the map information by specifying the current three-dimensional position.

16. The endoscope system according to claim 11, further comprising a target position calculating unit which calculates the target position from an endoscopic image picked up by an image pickup unit installed at the distal end of the insertion portion of the endoscope.

17. The endoscope system according to claim 11, wherein the bending control unit performs control so as to bend the bending portion by a relative angle corresponding to a differential value between a value in the direction calculated by the direction-of-the-target-position calculating unit and a value in the direction calculated by the direction-of-the-distal-end calculating unit.

18. The endoscope system according to claim 11, wherein the current three-dimensional position of the distal end of the insertion portion is detected based on positions of magnetic field generating coils installed in the insertion portion.

19. The endoscope system according to claim 11, wherein the map information is stored in the map information storage unit by being associated with identification information about the endoscope.

20. The endoscope system according to claim 11, further comprising an amount-of-twist detecting unit which detects an amount of twist of the insertion portion around an axial direction of the insertion portion.

* * * * *